United States Patent [19]

Kunz

[11] Patent Number: 4,546,179

[45] Date of Patent: Oct. 8, 1985

[54] PROCESS FOR PREPARING SULFONYLUREAS

[75] Inventor: Robert A. Kunz, Media, Pa.

[73] Assignee: E. I. Du Pont de Nemours and Company, Wilmington, Del.

[21] Appl. No.: 647,341

[22] Filed: Sep. 6, 1984

Related U.S. Application Data

[63] Continuation-in-part of Ser. No. 554,788, Nov. 23, 1983.

[51] Int. Cl.[7] .................. C07D 251/44; C07D 251/46; C07D 251/50; C07D 251/52

[52] U.S. Cl. ................................... 544/206; 544/207; 544/208; 544/209; 544/211; 544/212; 544/320; 544/321; 544/331; 544/332

[58] Field of Search ............... 544/211, 212, 320, 321, 544/331, 332, 206, 207, 208, 209; 71/93

[56] References Cited

U.S. PATENT DOCUMENTS

| | | | |
|---|---|---|---|
| 3,920,644 | 11/1975 | Handa et al. | 544/193 |
| 4,420,325 | 12/1983 | Sauers | 544/211 |
| 4,443,245 | 4/1984 | Meyer et al. | 544/211 |

Primary Examiner—John M. Ford

[57] ABSTRACT

Sulfonylureas are prepared by contacting a sulfonyl halide with an ammonium, phosphonium, sulfonium, or an alkali metal cyanate salt in the presence of an amine.

19 Claims, No Drawings

PROCESS FOR PREPARING SULFONYLUREAS

RELATED APPLICATION

This application is a continuation-in-part of my copending application U.S. Ser. No. 554,788 filed Nov. 23, 1983, for a Process for Preparing Sulfonylureas.

BACKGROUND OF THE INVENTION

This invention relates to a novel process for preparing sulfonylurea compounds by contacting a sulfonyl halide with an ammonium, phosphonium, sulfonium, or an alkali metal cyanate salt in the presence of an amine. The term "sulfonylurea" is used broadly herein to refer to a compound containing the sulfonylurea bridge, —SO₂NHCON—. Sulfonylureas prepared according to this invention are known to possess varying types of biological activity. For example, many are useful as anti-diabetic agents. See, for example, French Pat. No. 1,468,747 (1967); Wojciechowski, *Acta Pol. Pharm.* 19, No. 2:121-25 (1962); or Logemann et al., *Farmaco Ed. Sci.* 12, No. 7:586-93 (1957). A wide scope of sulfonylurea compounds has also been shown to possess herbicidal and plant growth regulant activity. A multitude of structural variations exist within this class of herbicides. See, for example, the compounds disclosed in U.S. Pat. Nos. 4,169,719, 4,127,405, 4,120,691, 4,221,585, 4,190,432, 4,225,337, 4,371,391, 4,339,266, 4,191,553, 4,305,884, 4,214,890, 4,339,267, 4,302,241, 4,342,587, 4,310,346, 4,293,330, 4,301,286, 4,370,479, 4,370,480, 4,368,067, 4,369,320, 4,348,219, 3,348,220, 4,333,760, 4,368,069, 4,394,506, 4,383,113, and 4,323,611 as well as European Patent Application No. 7,687, published Feb. 6, 1980, (EP-A) No. 44,212, published Jan. 20, 1982, (EP-A) No. 44,807, published Jan. 27, 1982, (EP-A) No. 44,808, published Jan. 27, 1982, (EP-A) No. 44,809, published Jan. 27, 1982, and (EP-A) No. 99,339, published Jan. 25, 1984, as well as South African Patent Application 838,416.

Sulfonylureas have, heretofore, been prepared by several synthetic methods. The most common method involves the reaction of an appropriate amine with a sulfonyl isocyanate as taught in U.S. Pat. No. 4,127,405. The necessary sulfonyl isocyanate can be prepared by several methods. This may be accomplished by reacting the corresponding sulfonamide with phosgene at reflux in a solvent such as chlorobenzene or xylene, according to the procedure of H. Ulrich and A. A. Y. Sayigh in *New Methods of Preparative Organic Chemistry*, Vol. VI, p. 223-241, Academic Press, New York and London, W. Foerst, Ed., or by the methods taught in U.S. Pat. No. 4,127,405 (1978), U.S. Pat. No. 4,238,671 (1980), and European Pat. No. 23,141. This method, however, has the disadvantage of requiring high reaction temperature, facilities for handling highly toxic phosgene, and special equipment for the recovery and/or scrubbing of the phosgene/HCl off-gas. The sulfonamide used in this phosgenation process can be prepared from ammonium hydroxide and a sulfonyl chloride as widely reported in the literature, e.g. Crossley et al., *J. Am. Chem. Soc.* 60, 2223 (1938).

Sulfonyl isocyanates have also been prepared by the reaction of sulfonyl chlorides with cyanate salts in the presence of nitrobenzene at 200° C. as taught in W. Guenter *Z. Chem.*, 9, 305 (1969). U.S. Pat. No. 2,974,164 to Franz discloses a similar process for preparing p-toluenesulfonyl isocyanate requiring temperatures of 150°-250° C. and a highly polar solvent such as nitrobenzene. The high temperature required for this reaction makes it unsuitable for many substituted sulfonyl isocyanates due to the instability of these isocyanates at high temperatures.

Japanese Patent Application 51-26816 discloses the preparation of alkyl and aryl sulfonyl isocyanates by the reaction of sulfonyl chlorides with cyanate salts in acetonitrile in the presence of phosphorous pentoxide and one or more catalysts such as lithium iodide, copper(II)-bromide, and quaternary ammonium salts.

Another known method for preparing sulfonylureas involves reaction of an amine with a carbamate, e.g. N-(benzenesulfonyl)phenyl carbamate, as taught in European Patent Application No. 44,807.

Due to the problems inherent in the processes described above for preparing sulfonylureas or the sulfonyl isocyanates used as intermediates in preparing sulfonylureas, and due to the increasingly important role played by sulfonylurea compounds as potent and environmentally safe herbicides and plant growth regulants, there is a clear need for new and economical processes for preparing these valuable compounds.

SUMMARY OF THE INVENTION

According to this invention a new process for preparing sulfonylurea compounds from easily obtainable starting materials has now been found. In this process, sulfonylureas of the formula $$RSO_2NHCNR_1R_2 \quad \overset{O}{\underset{\|}{}} \quad \text{I}$$

are prepared by contacting at reaction conditions, a sulfonyl halide of the formula $$RSO_2X \quad \text{II}$$

with an ammonium, phosphonium, sulfonium or an alkali metal cyanate salt $$M^+OCN^-$$

in the presence of an amine of the formula $$HNR_1R_2 \quad \text{III}$$

where
R is

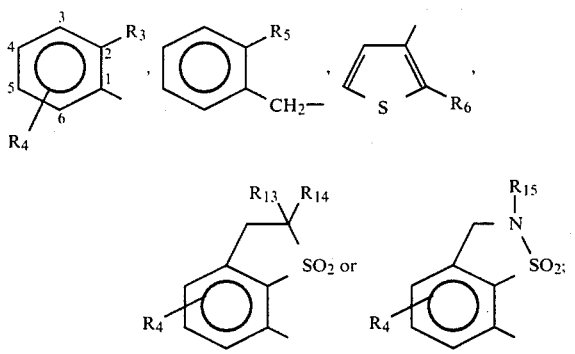

$R_3$ is F, Cl, Br, $C_1$-$C_4$ alkyl, $SO_2NR_7R_8$, $S(O)_nR_9$, $SO_2NCH_3(OCH_3)$, $CO_2R_{10}$, $OSO_2R_{11}$, $OR_{12}$, $NO_2$,

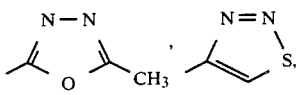, 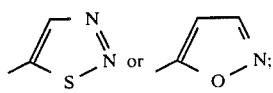

$R_4$ is H, F, Cl, Br, $CH_3$, $OCH_3$, $CF_3$, $NO_2$ or $CO_2R_{10}$ provided that when $R_4$ is $CO_2R_{10}$ then it is in the 6-position;

$R_5$ is Cl, $NO_2$ or $CO_2R_{11}$;

$R_6$ is Cl, Br, $SO_2NR_7R_8$, $S(O)_nR_{11}$ or $CO_2R_{11}$;

$R_7$ and $R_8$ are independently $C_1$–$C_3$ alkyl;

$R_9$ is $C_1$–$C_3$ alkyl or $C_1$–$C_3$ alkyl substituted by 1–3 atoms of F or Cl;

$R_{10}$ is $C_1$–$C_4$ alkyl, $CH_2CH_2OCH_3$, $CH_2CH_2Cl$ or $CH_2CH=CH_2$;

$R_{11}$ is $C_1$–$C_3$ alkyl;

$R_{12}$ is $C_1$–$C_4$ alkyl, $CH_2CH=CH_2$, $CH_2C\equiv CH$ or $C_1$–$C_3$ alkyl substituted with 1–3 atoms of F or Cl;

$R_{13}$ is H or $CH_3$;

$R_{14}$ is H or $CH_3$;

$R_{15}$ is $C_1$–$C_4$ alkyl;

n is 0 or 2;

X is Cl, F or Br;

M is an alkali metal or $R_aR_bR_cR_dL^+$;

$R_a$, $R_b$, $R_c$ and $R_d$ are independently $C_1$–$C_{18}$ alkyl, benzyl or phenyl provided that the total number of carbon atoms is not greater than 36;

L is N, P or S, provided that when L is S it is only substituted with $R_a$, $R_b$ and $R_c$;

$R_1$ is H or $CH_3$;

$R_2$ is

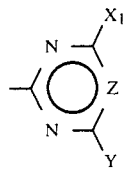

$X_1$ is $CH_3$, $OCH_3$, $OCH_2CH_3$, Cl or $OCF_2H$;

Y is $CH_3$, $OCH_3$, $CH(OCH_3)_2$, $OCH_2CF_3$, $NHCH_3$,

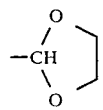

or $OCF_2H$; and

Z is CH or N;

provided that when $X_1$ is Cl, then Z is CH and Y is $OCH_3$ or $OCF_2H$ and when Y is $NHCH_3$ then $X_1$ is $OCH_3$ or $OCH_2CH_3$.

Preferred processes within the scope of this invention, due to their greater ease of operation and/or higher yield are the processes wherein:
 the reactants are combined in an aprotic solvent;
 the molar ratio of the sulfonyl halide to cyanate salt is in the range of 1:1 to 1:2.

More preferred for their greater ease of operation and/or higher yields are the processes of the preferred scope wherein:
 the solvent is methylene chloride, tetrahydrofuran or mixtures thereof;
 X is chlorine, and M is $R_aR_bR_cR_dL^+$, where L is nitrogen;
 the ratio of sulfonyl chloride to cyanate salt is in the range of 1:1 to 1.0:1.5.

Most preferred for their greatest ease of operation and/or highest yields are the processes of the preferred scope wherein:
 the solvent is acetonitrile, dimethylformamide, N-methylpyrrolidinone or mixtures thereof;
 X is chlorine, and M is sodium or potassium;
 the ratio of sulfonyl chloride to cyanate salt is in the range of 1.0 to 1.5.

Also preferred due to the utility of the endproducts as potent herbicides and/or plant growth regulants, are those processes wherein:

R is

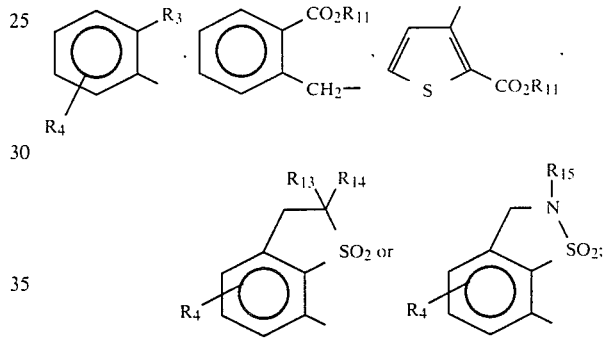

$R_3$ is Cl, $CH_3$, $SO_2N(CH_3)_2$, $S(O)_nR_9$, $CO_2R_{10}$, $OSO_2R_{11}$, $OR_{12}$ or $NO_2$;

$R_4$ is H, Cl, $CH_3$, $OCH_3$, $CF_3$ or $NO_2$;

$R_9$ is $C_1$–$C_3$ alkyl, $CF_3$, $CF_2H$ or $CF_2CF_2H$;

$R_{10}$ is $C_1$–$C_4$ alkyl;

$R_{11}$ is $C_1$–$C_3$ alkyl;

$R_{12}$ is $C_1$–$C_4$ alkyl, $CF_3$, $CF_2H$ or $CF_2CF_2H$;

$R_1$ is H;

X is Cl;

$R_a$, $R_b$, $R_c$ and $R_d$ are independently $C_2$–$C_4$ alkyl or benzyl; and M is sodium, potassium or $R_aR_bR_cR_dL^+$ where L is N.

Specifically preferred for the greatest utility of their products are those processes of the most preferred scope wherein the compounds of Formula I are:

2-[N-[(4-chloro-6-methoxypyrimidin-2-yl)aminocarbonyl]aminosulfonyl]benzoic acid, ethyl ester;

2-[N-[(4-methoxy-6-methyl-1,3,5-triazin-2-yl)aminocarbonyl]aminosulfonyl]benzoic acid, methyl ester;

2-[N-[(4,6-dimethylpyrimidin-2-yl)aminocarbonyl]aminosulfonyl]benzoic acid, methyl ester;

2-chloro-N-[(4-methoxy-6-methyl-1,3,5-triazin-2-yl)aminocarbonyl]benzenesulfonamide;

2-[N-[(4,6-dimethoxypyrimidin-2-yl)aminocarbonyl]aminosulfonylmethyl]benzoic acid, methyl ester;

3-[[(4-methoxy-6-methyl-1,3,5-triazin-2-yl)aminocarbonyl]aminosulfonyl]-2-thiophenecarboxylic acid, methyl ester;

2-hydroxy-N-[(4-methoxy-6-methyl-1,3,5-triazin-2-yl)aminocarbonyl]benzenesulfonamide, 1-propanesulfonate; and 5-chloro-2-[N-(4-methoxy-6-methyl-1,3,5-triazin-2-yl)aminocarbonyl]aminosulfonyl]benzoic acid, methyl ester.

The process of this invention is advantageous as it allows for the production of sulfonylureas, often in high yields, by reaction of sulfonyl halides and amines. As described previously, earlier known processes for preparing sulfonylureas involved reaction of sulfonyl isocyanates, prepared via a two-step process from sulfonyl chlorides, with amines. Thus, several process steps, including a difficult phosgenation step, are eliminated by the process of this invention.

DETAILED DESCRIPTION OF THE INVENTION

The sulfonyl halides of Formula II are either known or can be prepared by methods known to one skilled in the art. Aromatic sulfonyl chlorides may be prepared by diazotization of the appropriate amine with sodium nitrite in hydrochloric acid, followed by reaction of the diazonium salt with sulfur dioxide and cuprous chloride in acetic acid as described by H. L. Yale and F. Sowinski, *J. Org. Chem.*, 25, 1824 (1960). Other aromatic sulfonyl chlorides may be prepared by chlorosulfonation of a substituted aromatic in carbon tetrachloride [H. T. Clarke et al., *Org. Syn.*, Coll. Vol. I, 2nd Ed., 1941, p. 85)]. Certain sulfonyl chlorides are most easily prepared via heteroatom-facilitated lithiation, followed by sulfonation as taught in European Patent Application No. 73,562, published Mar. 9, 1983, and reviewed by H. W. Gschwend and H. R. Rodriguez in *Org. Reactions*, 26, 1 (1979).

The amines of Formula III are also either known or can be prepared by methods known in the art. For example, see "The Chemistry of Heterocyclic Compounds," Vol. 13 and 16, Interscience Publishers, Inc., New York and "The Chemistry of the Amino Group," Edited by S. Patai, Interscience Publishers, Inc., 1968, pages 37–77.

The process of this invention is best carried out in an aprotic solvent, such as methylene chloride, chloroform, o-dichlorobenzene, monochlorobenzene, acetonitrile, propionitrile, 1,2-dichloroethane, acetone, methyl ethyl ketone, dioxane, tetrahydrofuran, glyme, diglyme, nitrobenzene, dimethylacetamide, N-methylpyrrolidinone, dimethylformamide, or dimethylsulfoxide. In some cases the reaction may be run with no solvent and in other cases a mixture of two or more solvents may be advantageous. The preferred solvent for greater reactivity and ease of handling is acetonitrile, when an alkali metal cyanate is used in this process. Although, when $R_2$ is a triazine ($Z=N$), higher yields are often obtained by using dimethylformamide or N-methylpyrrolidinone as solvent.

When an ammonium, phosphonium, or sulfonium cyanate is used, the preferred solvents are methylene chloride, tetrahydrofuran, or mixtures of these two solvents. The combination of tetraalkyl ammonium cyanate in methylene chloride solvent at ambient temperature is particularly useful for thermally labile sulfonyl halides, such as 2,6-bis(methoxycarbonyl)benzenesulfonyl chloride.

The cyanate salts used in this invention are substituted ammonium, phosphonium, and sulfonium cyanates, and also alkali metal cyanates such as sodium and potassium cyanate. The preferred salts for greater reactivity and availability are sodium and potassium cyanate, and tetraalkyl ammonium cyanates such as tetrabutylammonium cyanate. The ammonium, phosphonium, and sulfonium cyanates can be prepared by ion exchange procedures described in A. Gallesit and T. M. Brown, *Synthesis in Inorganic and Metal-Organic Chemistry*, 2(4), 273–5 (1975) and H. Kobler, R. Munz, G. A. Gasser, and G. Simchen, *Liebigs Ann. Chem.*, 1978, 1937–1945. Mixtures of alkali metal cyanates and ammonium, phosphonium, or sulfonium cyanates may be employed. In some cases the addition of a tertiary amine such as DABCO, or a crown ether such as 18-crown-6, will lead to increased yields of the sulfonylurea products.

The reaction temperature should be in the range of about 0° C. to about 200° C. For most reactions, the range of about 20° to 150° C. provides good results. The preferred temperature for optimum yields and ease of operation is about 25°–80° C. If a temperature higher than the atmospheric boiling point of the solvent is desired, the reaction may be run under pressure at the desired temperature.

The reaction time is determined by the reactivity of the starting materials. In some cases, the reaction is complete after a few minutes while in other cases a reaction time up to about 8 hours normally is advantageous. The preferred reaction time is normally in the range of 0.5 to 4 hours.

The relative ratio of reactants is determined by their relative costs and reactivity. The sulfonyl halide and amine are normally used in about a 1:1 ratio and the cyanate salt is used in excess. Ratios of sulfonyl halide to cyanate salt can be 1:1 to 1:10, although for ease of isolating product a ratio of 1:1 to 1:2 is preferred.

The resulting sulfonylurea can be isolated by several methods, depending on the solvent, the solubility of the product and the presence of by-products. In some cases, the reaction can be diluted with water and filtered to give essentially pure sulfonylurea. In other cases, the product can be dissolved in dilute base, filtered, and the filtrate acidified to reprecipitate the product. In still other cases, the reaction can be filtered hot, the solvent removed from the filtrate by distillation, and the resulting product further purified to give the desired sulfonylurea.

It will be obvious to one skilled in the art that the process of the instant invention may be used to prepare a wide variety of useful sulfonylureas, in addition to the sulfonylureas described in Formula I. The only limitation on the sulfonylureas that may be prepared by the process of the instant invention is that the amine chosen must not react with the sulfonyl halide selected, under the reaction conditions selected, to generate significant quantities of by-product sulfonamide.

The process of this invention is further illustrated by the following examples. All temperatures are in degrees Centigrade.

EXAMPLE 1

Preparation of 2-[[(4,6-Dimethylpyrimidin-2-yl)aminocarbonyl]aminosulfonyl]benzoic acid, methyl ester A slurry of 7.0 grams (0.057 moles) of 4,6-dimethyl-2-pyrimidinamine, 6.0 grams (0.092 moles) sodium cyanate, and 13.5 grams (0.057 moles) 2-carbomethoxybenzenesulfonyl chloride in 60 ml acetonitrile was stirred 1 hour at reflux (81°). The reaction was diluted with 60 ml water, allowed to cool to room temperature and filtered. The solid was washed with 20 ml water and dried. There was obtained 16.0 grams (77.0% of theory) of the title compound. The product was 98% pure as assayed by high pressure liquid chromatography. The m.p. and IR spectrum of the title compound were identical to those of an authentic sample prepared as described in U.S. Pat. No. 4,394,506.

EXAMPLE 2

Preparation of 2-Chloro-N-[(4,6-dimethylpyrimidin-2-yl)aminocarbonyl]benzenesulfonamide A slurry of 23.8 g (0.10 mole) 2-chlorobenzenesulfonyl chloride, 16.2 g (0.2 mole) potassium cyanate, 15.5 g (0.11 moles) 4,6-dimethyl-2-pyrimidinamine in 150 ml acetonitrile was stirred at reflux for 5 hours. The reaction was cooled to 25° and filtered. The solids were dissolved in water, filtered, and the filtrate acidified to give a solid A. The reaction filtrate was distilled in vacuo to remove solvent. The residue and Solid A were combined, dissolved in 200 ml of 5% sodium hydroxide and extracted with methylene chloride. The aqueous layer was then acidified, the solids collected, washed with water and dried to give 18.9 g (50.6% of theory) of the title compound. The m.p. and IR spectrum of the title compound were identical to those of an authentic sample prepared as described in U.S. Pat. No. 4,169,719.

EXAMPLE 3

Preparation of 2-[[(4-Methoxy-6-methyl-1,3,5-triazin-2-yl)aminocarbonyl]aminosulfonyl]benzoic acid, methyl ester A slurry of 10.0 grams (0.042 moles) of 2-carbomethoxybenzenesulfonyl chloride, 5.0 grams (0.0357 moles) 4-methoxy-6-methyl-1,3,5-triazin-2-amine and 6.0 grams (0.092 moles) sodium cyanate in 60 ml N-methylpyrrolidinone was stirred 2 hours at 80° C. The reaction was cooled to 25° C., diluted with 200 ml saturated sodium bicarbonate solution, and filtered. The filtrate was acidified with dilute hydrochloric acid and the product was collected by filtration and dried to give the title compound in 55% yield. The IR spectrum of the title compound was identical to that of an authentic sample prepared as taught in U.S. Pat. No. 4,383,113.

EXAMPLE 4

Preparation of 3-Chloro-2-[[(4-methoxy-6-methylpyrimidin-2-yl)aminocarbonyl]aminosulfonyl]benzoic acid, methyl ester A solution of N,N,N-tributyl-1-butanaminium cyanate (1.42 g, 5.0 mmol) in dry dichloromethane (12 mL) was added over 1.25 hours to a stirred mixture of methyl 3-chloro-2-chlorosulfonylbenzoate (1.35 g, 5.0 mmol) and 4-methoxy-6-methyl-2-pyrimidinamine (0.83 g, 6.0 mmol) in a mixture of dry dichloromethane (11 mL) and dry tetrahydrofuran (11 mL) at room temperature. The mixture was stirred 4 hours more and was then diluted with dichloromethane (100 mL), washed with aqueous sulfuric acid (1N, 4×50 mL), and dried (Na$_2$SO$_4$). The solution was diluted with 1-chlorobutane and evaporated. The residue was dissolved in dichloromethane, diluted with 1-chlorobutane and evaporated to leave a gummy foam (1.9 g). This was dissolved in a mixture of dichloromethane and 1-chlorobutane and allowed to stand nine days at room temperature. The mixture was then filtered, and the filtrate was evaporated to leave a colorless foam (1.7 g). A portion (1.4 g) was dissolved in dichloromethane (ca. 15 mL) and extracted with aqueous sodium carbonate solution (5%, 10 mL). This aqueous extract was in turn washed with dichloromethane and hexanes, cooled with the aid of an ice-bath and acidified to pH <1 with concentrated hydrochloric acid. A white crystalline solid formed. It was rinsed with ice-cold dilute hydrochloric acid and dried. The product was obtained as a white crystalline powder (0.3 g, ca. 14% of theory uncorrected by assay) melting at 90°–95° C. with decomposition. PMR (CDCl$_3$, 200 MHz): δ14.00 (very broad s, 1H, SO$_2$NHCO); 7.50–7.65 (m, 3H, Ar—H and CONH—Het); 7.35–7.45 (m, 1H, Ar—H); 6.32 (s, 1H, Het 5-H); 3.99 (s, 3H, Het—OCH$_3$); 3.97 (s, 3H, CO$_2$CH$_3$) and 2.44 (s, 3H, Het—CH$_3$). Estimation based upon the PMR spectrum indicated the material to be 70% sulfonylurea. IR (Nujol): 1735 (vs, ester and urea C=O's) cm$^{-1}$.

EXAMPLE 5

Preparation of 2-[[(4,6-Dimethoxypyrimidin-2-yl)aminocarbonyl]aminosulfonyl]-1,3-benzenedicarboxylic acid, dimethyl ester A solution of N,N,N-tributyl-1-butanaminium cyanate (1.42 g, 5.0 mmol) in dry dichloromethane (12 mL) was added over 1.75 hours to a stirred mixture of dimethyl 2-chlorosulfonyl-1,3-benzenedicarboxylate (1.46 g, 5.0 mmol) and 4,6-dimethoxy-2-pyrimidinamine (0.93 g, 6.0 mmol) in a mixture of dry dichloromethane (11 mL) and dry tetrahydrofuran (11 mL) at room temperature. The mixture was stirred 4 hours more and was then diluted with dichloromethane (100 mL), washed with aqueous sulfuric acid (1N, 4×50 mL) and dried (Na$_2$SO$_4$). Evaporation of the solvent, dissolution of the residue in 1,2-dichloroethane, and reevaporation left a yellow oil (2.3 g). This was dissolved in CH$_2$Cl$_2$ and chromatographed on a column of silica gel using 4:1, then 3:1, and then 2:1 dichloromethane-ether all with 2 mL/L acetic acid as eluant. Fractions containing product (R$_f$=0.33, 4:1 CH$_2$Cl$_2$—Et$_2$O+2 mL/L AcOH, UV) were diluted with toluene and evaporated to leave a solid. This was dissolved in dichloromethane and diluted with 1-chlorobutane. Evaporation of the solvent left a crystalline solid. This was slurried in hexanes, collected, rinsed with 1-chlorobutane and hexanes, and dried. The product was obtained as a fine white crystalline powder (0.21 g, 9.2% of theory) melting at 164°–167° C. with decomposition. PMR (CDCl$_3$, 200 MHz): δ12.57 (br s, 1H, SO$_2$NHCO); 7.65–7.72 (m, 3H, Ar—H); 7.21 (br s, 1H, CONH—Het); 5.80 (s, 1H, Het 5-H); 3.98 (s, 6H, Het—OCH$_3$) and 3.90 (s, 6H, CO$_2$CH$_3$). IR(Nujol): 1731 (vs, ester C=O), 1700 (s, urea C=O) cm$^{-1}$.

What is claimed is:

1. A process for preparing a compound of the formula

comprising contacting at reaction conditions, a sulfonyl halide of the formula

RSO$_2$X with an ammonium, phosphonium, sulfonium or an alkali metal cyanate salt of the formula

M$^+$OCN$^-$ in the presence of an amine of the formula

HNR$_1$R$_2$, where
R is

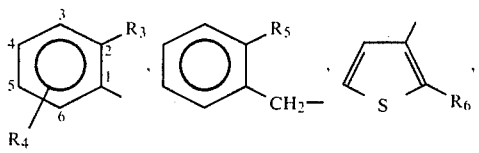

R$_3$ is F, Cl, Br, C$_1$-C$_4$ alkyl, SO$_2$NR$_7$R$_8$, S(O)$_n$R$_9$, SO$_2$NCH$_3$(OCH$_3$), CO$_2$R$_{10}$, OSO$_2$R$_{11}$, OR$_{12}$, NO$_2$,

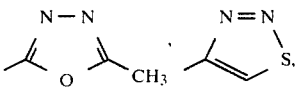

R$_4$ is H, F, Cl, Br, CH$_3$, OCH$_3$, CF$_3$, NO$_2$ or CO$_2$R$_{10}$ provided that when R$_4$ is CO$_2$R$_{10}$ then it is in the 6-position;
R$_5$ is Cl, NO$_2$ or CO$_2$R$_{11}$;
R$_6$ is Cl, Br, SO$_2$NR$_7$R$_8$, S(O)$_n$R$_{11}$ or CO$_2$R$_{11}$;
R$_7$ and R$_8$ are independently C$_1$-C$_3$ alkyl;
R$_9$ is C$_1$-C$_3$ alkyl or C$_1$-C$_3$ alkyl substituted by 1-3 atoms of F or Cl;
R$_{10}$ is C$_1$-C$_4$ alkyl, CH$_2$CH$_2$OCH$_3$, CH$_2$CH$_2$Cl or CH$_2$CH=CH$_2$;
R$_{11}$ is C$_1$-C$_3$ alkyl;
R$_{12}$ is C$_1$-C$_4$ alkyl, CH$_2$CH=CH$_2$, CH$_2$C≡CH or C$_1$-C$_3$ alkyl substituted with 1-3 atoms of F or Cl;
R$_{13}$ is H or CH$_3$;
R$_{14}$ is H or CH$_3$;
R$_{15}$ is C$_1$-C$_4$ alkyl;
n is 0 or 2;
X is Cl, F or Br;
M is an alkali metal or R$_a$R$_b$R$_c$R$_d$L$^+$;
R$_a$, R$_b$, R$_c$ and R$_d$ are independently C$_1$-C$_{18}$ alkyl, benzyl or phenyl provided that the total number of carbon atoms is not greater than 36;
L is N, P or S, provided that when L is S it is only substituted with R$_a$, R$_b$ and R$_c$;
R$_1$ is H or CH$_3$;

R$_2$ is

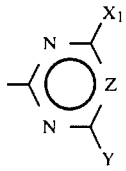

X$_1$ is CH$_3$, OCH$_3$, OCH$_2$CH$_3$, Cl or OCF$_2$H;
Y is CH$_3$, OCH$_3$, CH(OCH$_3$)$_2$, OCH$_2$CF$_3$, NHCH$_3$,

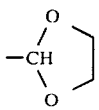

or
OCF$_2$H; and
Z is CH or N;
provided that when X$_1$ is Cl, then Z is CH and Y is OCH$_3$ or OCF$_2$H and when Y is NHCH$_3$ then X$_1$ is OCH$_3$ or OCH$_2$CH$_3$.

2. The process of claim 1 where the reactants are combined in an aprotic solvent; the molar ratio of the sulfonyl halide to cyanate salt is in the range of 1:1 to 1:2.

3. The process of claim 2 where the the solvent is methylene chloride, tetrahydrofuran or mixtures thereof; X is chlorine, and M is R$_a$R$_b$R$_c$R$_d$L$^+$, where L is nitrogen; and the ratio of sulfonyl chloride to cyanate salt is in the range of 1:1 to 1.0:1.5.

4. The process of claim 2 where the solvent is acetonitrile, dimethylformamide, N-methylpyrrolidinone or mixtures thereof; X is chlorine, and M is sodium or potassium; the ratio of sulfonyl chloride to cyanate salt is in the range of 1.0 to 1.5.

5. The process of claim 1 where R is

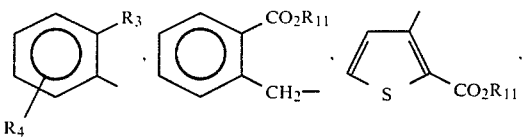

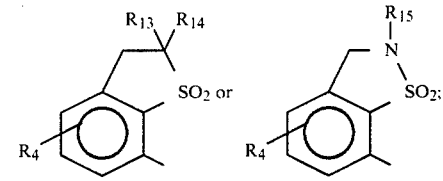

R$_3$ is Cl, CH$_3$, SO$_2$N(CH$_3$)$_2$, S(O)$_n$R$_9$, CO$_2$R$_{10}$, OSO$_2$R$_{11}$, OR$_{12}$ or NO$_2$;
R$_4$ is H, Cl, CH$_3$, OCH$_3$, CF$_3$ or NO$_2$;
R$_9$ is C$_1$-C$_3$ alkyl, CF$_3$, CF$_2$H or CF$_2$CF$_2$H;
R$_{10}$ is C$_1$-C$_4$ alkyl;
R$_{11}$ is C$_1$-C$_3$ alkyl;
R$_{12}$ is C$_1$-C$_4$ alkyl, CF$_3$, CF$_2$H or CF$_2$CF$_2$H;
R$_1$ is H;
X is Cl;
R$_a$, R$_b$, R$_c$ and R$_d$ are independently C$_2$-C$_4$ alkyl or benzyl; and
M is sodium, potassium or R$_a$R$_b$R$_c$R$_d$L$^+$ where L is N.

6. The process of claim 5 where R is

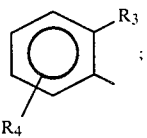

$R_3$ is $CO_2R_{10}$;
$R_4$ is H;
$R_{10}$ is $CH_2CH_3$;
$X_1$ is Cl;
Y is $OCH_3$; and
Z is CH.

7. The process of claim 5 where R is

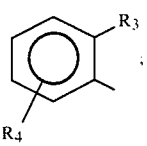

$R_3$ is $CO_2R_{10}$;
$R_4$ is H;
$R_{10}$ is $CH_3$;
$X_1$ is $OCH_3$;
Y is $CH_3$; and
Z is N.

8. The process of claim 5 where R is

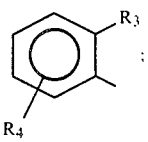

$R_3$ is $CO_2R_{10}$;
$R_4$ is H;
$R_{10}$ is $CH_3$;
$X_1$ is $CH_3$;
Y is $CH_3$; and
Z is CH.

9. The process of claim 5 where R is

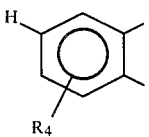

$R_3$ is Cl;
$R_4$ is H;
$X_1$ is $OCH_3$;
Y is $CH_3$; and
Z is N.

10. The process of claim 5 where R is

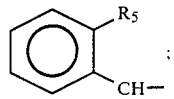

$R_5$ is $CO_2R_{11}$;
$R_{11}$ is $CH_3$;
$X_1$ is $OCH_3$;
Y is $OCH_3$; and
Z is CH.

11. The process of claim 5 where R is

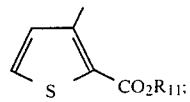

$R_{11}$ is $CH_3$;
$X_1$ is $CH_3$;
Y is $OCH_3$; and
Z is N.

12. The process of claim 5 where R is

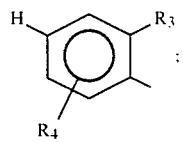

$R_3$ is $OSO_2R_{11}$;
$R_4$ is H;
$R_{11}$ is n-$C_3H_7$;
$X_1$ is $CH_3$;
Y is $OCH_3$; and
Z is N.

13. The process of claim 4 where R is

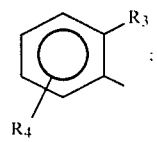

$R_3$ is $CO_2R_{10}$;
$R_4$ is H;
$R_{10}$ is $CH_2CH_3$;
$X_1$ is Cl;
Y is $OCH_3$; and
Z is CH.

14. The process of claim 4 where R is

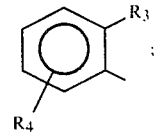

$R_3$ is $CO_2R_{10}$;
$R_4$ is H;

$R_{10}$ is $CH_3$;
$X_1$ is $OCH_3$;
Y is $CH_3$; and
Z is N.

15. The process of claim 4 where R is

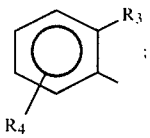

$R_3$ is $CO_2R_{10}$;
$R_4$ is H;
$R_{10}$ is $CH_3$;
$X_1$ is $CH_3$;
Y is $CH_3$; and
Z is CH.

16. The process of claim 4 where R is

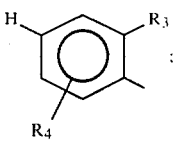

$R_3$ is Cl;
$R_4$ is H;
$X_1$ is $OCH_3$;
Y is $CH_3$; and
Z is N.

17. The process of claim 4 where R is

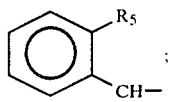

$R_5$ is $CO_2R_{11}$;
$R_{11}$ is $CH_3$;
$X_1$ is $OCH_3$;
Y is $OCH_3$; and
Z is CH.

18. The process of claim 4 where R is

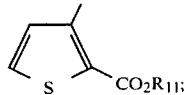

$R_{11}$ is $CH_3$;
$X_1$ is $CH_3$;
Y is $OCH_3$; and
Z is N.

19. The process of claim 4 where R is

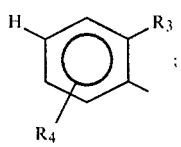

$R_3$ is $OSO_2R_{11}$;
$R_4$ is H;
$R_{11}$ is $n-C_3H_7$;
$X_1$ is $CH_3$;
Y is $OCH_3$; and
Z is N.

* * * * *